United States Patent [19]

Brimhall et al.

[11] Patent Number: 5,582,597
[45] Date of Patent: Dec. 10, 1996

[54] ROTARY RAM COLLET LOCK NEEDLE POINT GUARD

[75] Inventors: Greg L. Brimhall, West Jordan; Thomas M. Yuranko, Salt Lake City, both of Utah

[73] Assignee: Becton Dickinson and Company, Franklin Lakes, N.J.

[21] Appl. No.: 501,265

[22] Filed: Jul. 11, 1995

[51] Int. Cl.[6] ................................................. A61M 5/32
[52] U.S. Cl. .......................... 604/192; 604/198; 604/263
[58] Field of Search .................................. 604/192, 198, 604/110, 263, 162, 163, 171

[56] References Cited

U.S. PATENT DOCUMENTS

| | | | |
|---|---|---|---|
| 5,104,384 | 4/1992 | Parry | 604/192 |
| 5,292,314 | 3/1994 | D'Alessio et al. | 604/198 |
| 5,389,085 | 2/1995 | D'Alessio et al. | 604/198 |
| 5,415,645 | 5/1995 | Friend et al. | 604/110 |
| 5,447,501 | 9/1995 | Karlsson et al. | 604/263 X |

*Primary Examiner*—John D. Yasko
*Attorney, Agent, or Firm*—Eric M. Lee, Esq.

[57] ABSTRACT

A needle point guard having a movable collet to lock the needle in place in the shielded position is provided. The needle point guard of this invention includes a housing, a collet, a rotary ram, a threaded cam fixed to the rotary ram, a spring disposed between the rotary ram and the housing and a trigger catch to hold the threaded cam in place against the force of the spring. The spring is wound when the needle is in the unshielded position. When the needle is withdrawn into the needle point guard, the trigger catch pivots to allow the spring to rotate the threaded cam. This rotation is translated into axial motion by the treads on the threaded cam and threads formed on the inside of the housing. This axial motion forces an annular flange on the collet to bite down on the needle, to thus hold the needle in place in the shielded position.

7 Claims, 5 Drawing Sheets

ROTARY RAM COLLET LOCK NEEDLE POINT GUARD

BACKGROUND OF THE INVENTION

This invention relates to a needle point guard that can be used with needles such as hypodermic needles, catheter introducer needles, and needles used with blood collection assemblies.

Sharp needles are typically used in health care procedures to inject fluid into or withdraw fluid from a patient or to introduce a device such as an intravenous catheter in a patient. After use these needles are disposed of to prevent their reuse. Unfortunately, in emergency situations or through neglect or inattention on the part of health care workers, used needles may stick other people in the area before the used needle is properly discarded. These needle sticks are distracting and uncomfortable at best. In addition, recently there has been great concern over accidental needle sticks because of the advent of certain diseases such as hepatitis and AIDS. Such diseases can be transmitted by the exchange of body fluids from an infected person to another person.

Thus there is a need for a guard that will shield the sharp distal tip of a needle after use. Because of this need, some needle guards have already been designed. Unfortunately, some of these designs are inadequate because they are bulky, difficult to use or require special features on the needle to be operative.

SUMMARY OF THE INVENTION

It is therefore an object of this invention to provide a needle point guard that effectively shields the sharp distal tip of the needle after use.

It is another object of this invention to provide a needle point guard that is not bulky.

It is yet another object of this invention to provide a needle point guard that is simple to use.

It is still another object of this invention to provide a needle point guard that does not require any special features on the needle for the needle point guard to be operative.

The needle point guard of this invention includes a housing having an open proximal end and an open distal end through which a needle extends, a collet disposed in the housing adjacent to the open proximal end, a generally hollow rotary ram disposed in the housing adjacent to the collet, the rotary ram having a threaded cam at its distal end, a spring operably disposed between the rotary ram and the housing, and a trigger catch adapted to maintain the threaded cam and rotary ram in a distal position when a needle extends through the housing.

Prior to activation of the needle point guard of this invention, the needle extends through the housing with the sharp distal tip of the needle extending beyond the open distal end of the housing. In this condition, the rotary ram is in a distal position to allow slight distal movement of the collet so the sharp distal tip of the needle can be slid proximally into the needle point guard after use. The spring is wound to exert a rotary force on the rotary ram. However, the trigger catch which is held in place by the needle shaft holds the threaded cam in position against the force of the spring. When the needle is withdrawn proximally after use such that the sharp distal tip of the needle is withdrawn into the housing out of contact with the trigger catch, the trigger catch pivots away from contact with the threaded cam. The spring thus rotates the rotary ram and the threaded cam. Threads provided on the inside of the housing engage the threads on the threaded cam to convert the rotary motion of the rotary ram into a linear motion. The rotary ram is thus urged in the proximal direction to force the collet proximally. The collet includes an outwardly extending annular flange that extends through the open proximal end of the housing. Proximal movement of the collet forces the annular flange of the collet to bind on the needle and hold the needle in place so the sharp distal tip of the needle remains shielded inside the housing.

BRIEF DESCRIPTION OF THE DRAWINGS

The above and other objects and advantages of the invention will be apparent upon consideration of the following drawings and detailed description. The preferred embodiments of the present invention are illustrated in the appended drawings in which like reference numbers refer to like elements and in which.

DETAILED DESCRIPTION OF THE INVENTION

Figure 1:
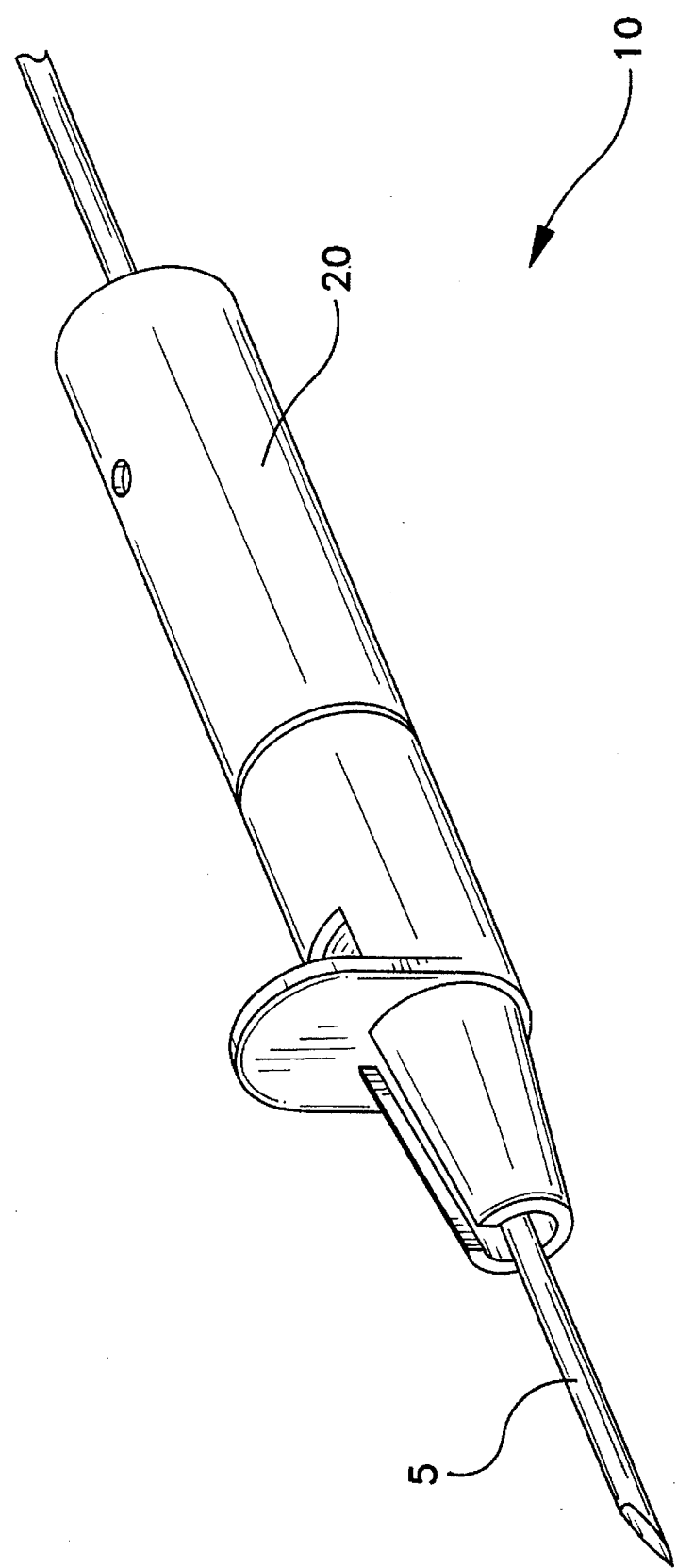
FIG. 1 is a perspective view of the needle point guard of this invention located on a distal portion of a needle.
Figure 2:
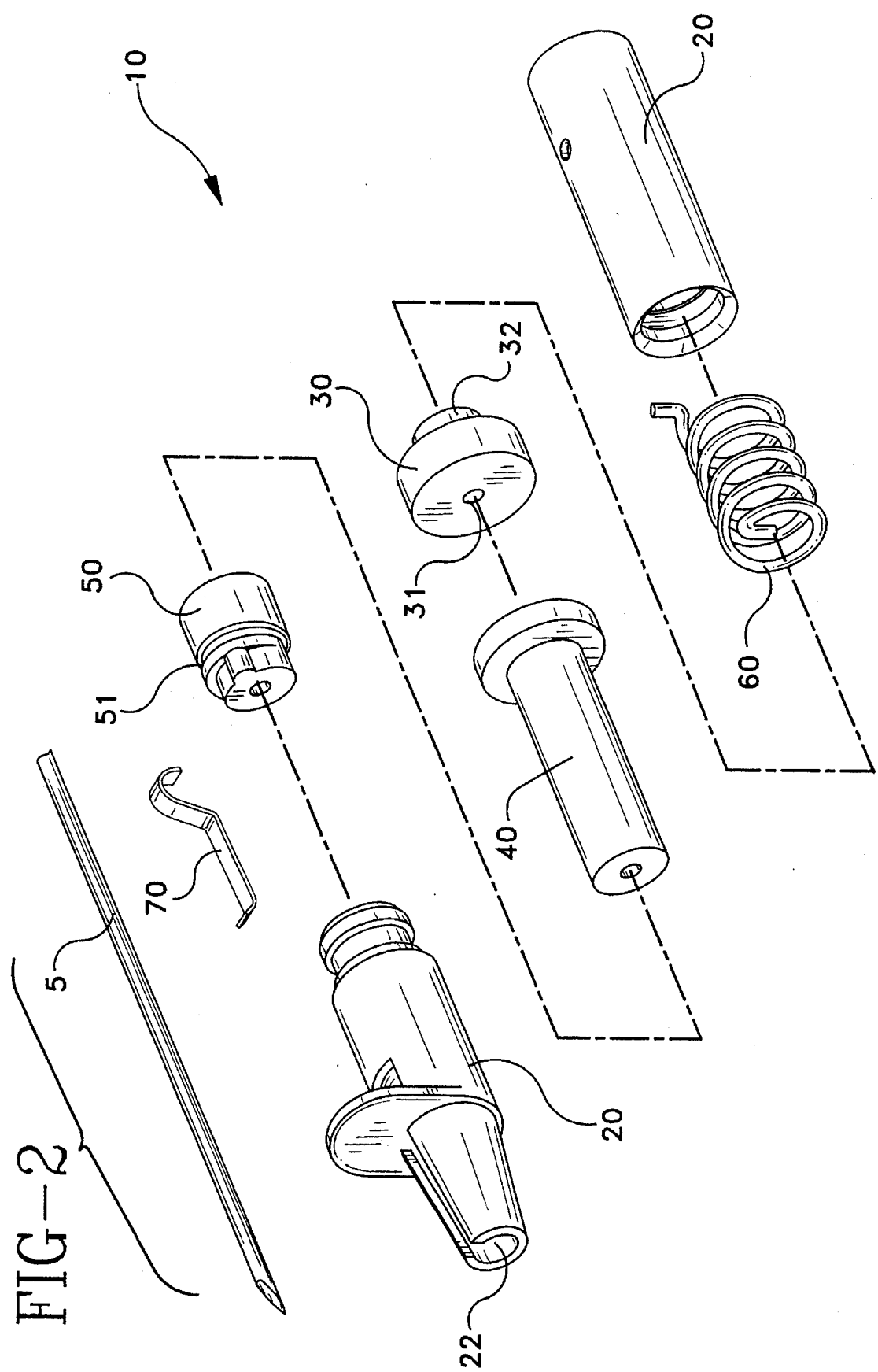
FIG. 2 is an exploded perspective view of the needle point guard of this invention.

The needle point guard 10 of this invention can be used on any type of needle where it is desirable to shield the sharp distal tip after use. The needle point guard 10 includes a housing 20 that fits over the needle 5 and has an open proximal end 21 and an open distal end 22 to allow needle 5 to extend therethrough. As shown in the FIGS., housing 20 includes a proximal portion and a distal portion.

A movable collet 30 is located inside housing 20 adjacent to open proximal end 21. Collet 30 has an annular cross-section with an inner hole 31 to allow needle 5 to extend through it. Inner hole 31 of collet 30 should have a diameter large enough to allow needle 5 to freely move through it. Collet 30 also includes a flexible annular flange 32 extending from the proximal side of collet 30. In the unshielded position of needle point guard 10 shown in FIG. 3, the body of collet 30 is spaced from the proximal end of housing 20 and annular flange 32 preferably extends partially into open proximal end 21 of housing 20. When needle point guard 10 is in the shielded position shown in FIG. 4, the body of collet 30 is preferably abutting the proximal end of housing 20 and annular flange 32 is forced together by the angled sides of open proximal end 21 of housing 20 to narrow the proximal end of inner hole 31. In this manner, annular flange 32 bites onto needle 5 to prevent axial movement of needle 5.

Figure 3:
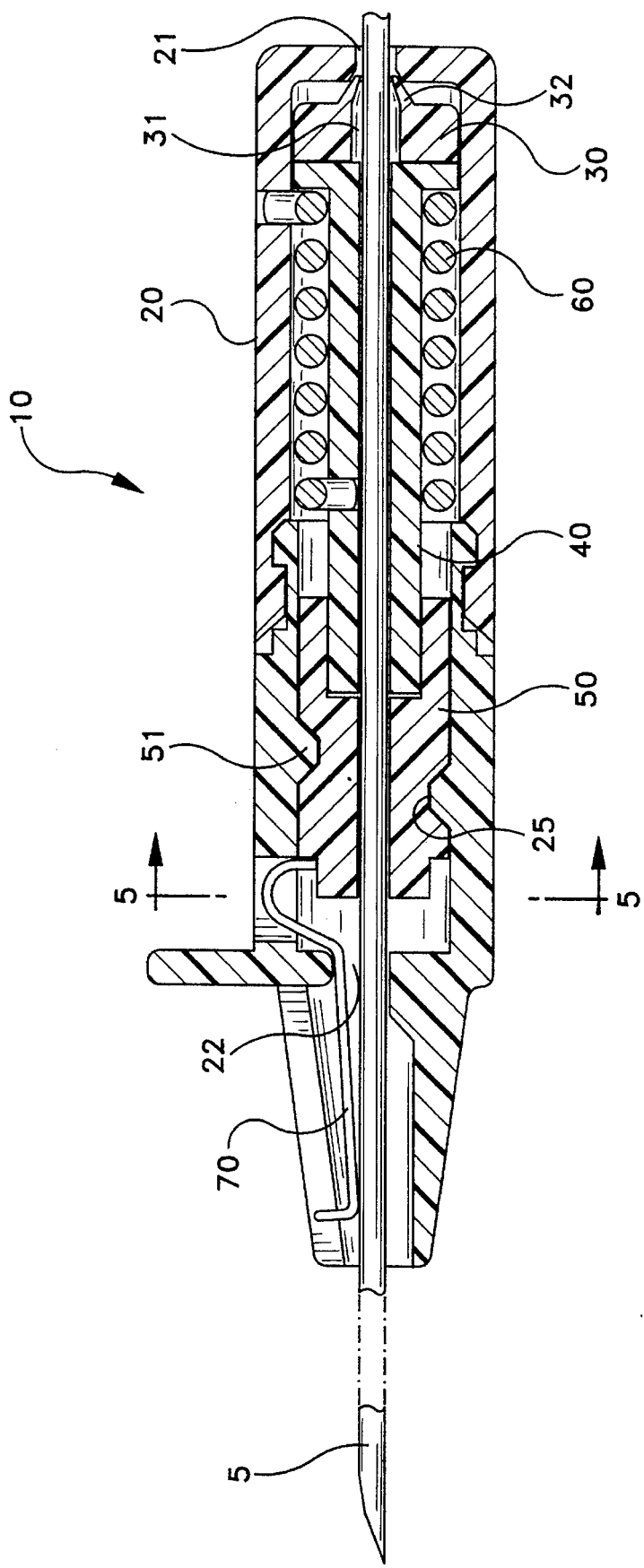
FIG. 3 is a cross-sectional view of the needle point guard of this invention with the rotary ram in the distal position.
Figure 4:
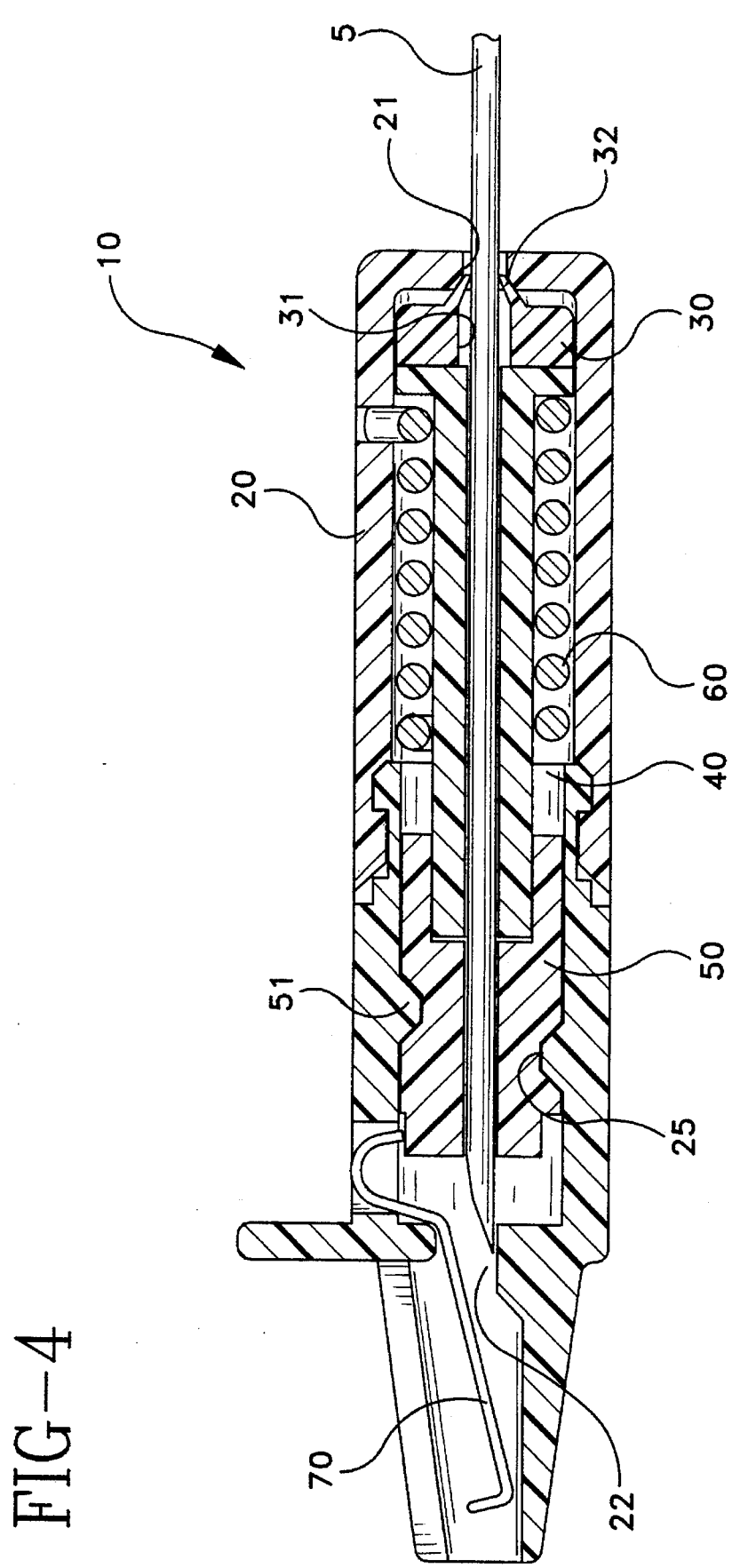
FIG. 4 is a cross-sectional view of the needle point guard of this invention with the rotary ram in the proximal position.
Figure 5:
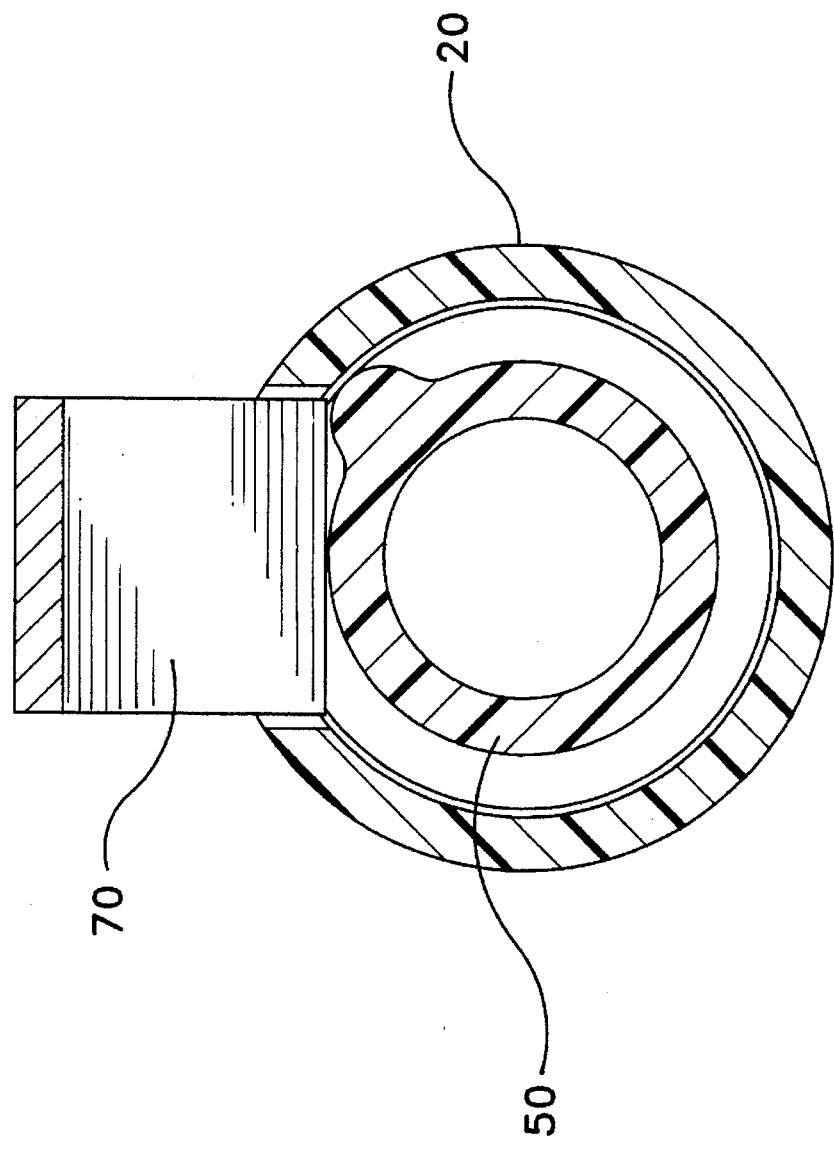
FIG. 5 is an end view of the needle point guard of this invention taken along line 5—5 of FIG. 3.

Needle point guard 10 also includes a mechanism to move collet 30 between the position shown in FIG. 3 to the position shown in FIG. 4. This mechanism includes a rotary ram 40, a threaded cam 50 and a spring 60. Rotary ram 40 is hollow to allow needle 5 to freely pass therethrough. Threaded cam 50 is connected to the distal end of rotary ram 40. Spring 60 is located about rotary ram 40 with one end fixed to rotary ram 40 and the other end fixed to housing 20.

Threaded cam 50 is also hollow to allow needle 5 to freely pass therethrough. The exterior surface of threaded cam 50 is formed with threads 51 therein that mate with threads 25 formed on a portion of the internal surface of housing 20. These threads 51 and 25 are oriented such that rotation of threaded cam 50 results in axial movement of threaded cam 50. Spring 60 can provide the rotation to threaded cam 50 by being initially wound when needle point guard 10 is in the unshielded position show in FIG. 3. Care must be taken to ensure that spring 60 is initially wound in the appropriate direction and threads 51 and 25 are oriented appropriately so that when spring 60 unwinds it rotates threaded cam 50 in the correct direction so that threads 51 and 25 force threaded cam 50 in the proximal direction. This in turn will force rotary ram 40 in the proximal direction to urge collet 30 into the abutting relationship with the proximal end of housing 20 shown in FIG. 4.

A latch mechanism is provided with needle point guard 10 to hold threaded cam 50 in a position against the rotational bias of spring 60 when spring 60 has been initially wound. The latch mechanism includes a pivotable trigger catch 70 that cooperates with threaded cam 50 and needle 5. When needle 5 extends past open distal end 22 of housing 20, trigger catch 70 rests on the outside of needle 5. In this position, the proximal end of trigger catch 70 abuts a cam on threaded cam 50 to prevent rotation of threaded cam 50. When needle 5 is withdrawn into needle point guard 10 so that trigger catch 70 no longer contacts needle 5, the distal end of trigger catch 70 will pivot to move the proximal end of trigger catch 70 away from threaded cam 50. With trigger catch 70 no longer in abutting relationship to threaded cam 50, spring 60 cam rotates threaded cam 50 to cause threaded cam 50 and rotary ram 40 to move proximally so annular flange 32 on collet 30 will bite down on needle 5. This prevents axial movement of needle 5 and thus needle point guard 10 holds needle 5 in the shielded position shown in FIG. 4.

Thus it is seen that a needle point guard is provided that effectively shields the sharp distal tip of the needle after use, that is not bulky, is simple to use and does not require any special feature on the needle for it to be operative.

We claim:

1. A needle point guard, comprising:
   a generally hollow housing having a proximal end and a distal end with an inside surface having threads formed on at least a portion of the inside surface;
   a movable ram disposed inside the housing and having a proximal portion and a distal portion with external threads formed thereon that engage with the threads formed on the inside surface of the housing;
   a spring disposed about the ram between the ram and the housing and adapted to impart rotation to the ram; and
   a movable trigger catch adjacent to the ram to hold the ram against rotation by the spring.

2. The needle point guard of claim 1 further comprising a collet disposed inside the housing between the proximal portion of the ram and the proximal end of the housing wherein the collet includes an annular flange adapted to engage a needle extending into the needle point guard when the collet is moved in a proximal direction.

3. The needle point guard of claim 2 wherein the distal portion of the ram further includes a cam thereon that engages with the trigger catch to hold the ram against the force of the spring.

4. A needle point guard, comprising:
   a generally hollow housing having a proximal end and a distal end;
   a movable ram disposed in the housing;
   a means for causing the movable ram to rotate;
   a means for translating rotation of the movable ram to a proximal axial movement of the movable ram so that rotation of the movable ram results in a proximal axial movement of the movable ram; and
   a means for preventing axial movement of a needle after the needle is withdrawn into the needle point guard.

5. The needle point guard of claim 4 further including a means for temporarily holding the movable ram against the force of the spring.

6. A needle point guard, comprising:
   a generally hollow housing having a proximal end and a distal end with an inside surface having threads formed on at least a portion of the inside surface;
   a movable ram disposed inside the housing and having a proximal end and a distal end;
   a cam connected to the distal end of the ram with external threads formed thereon that engage with the threads formed on the inside surface of the housing;
   a spring disposed about the ram between the ram and the housing and adapted to impart rotation to the ram; and
   a movable trigger catch adjacent to the cam to hold the cam against rotation by the spring.

7. The needle point guard of claim 6 further comprising a collet disposed inside the housing between the proximal end of the ram and the proximal end of the housing wherein the collet includes an annular flange adapted to engage a needle extending into the needle point guard when the collet is moved in a proximal direction.

* * * * *